United States Patent [19]

Mikler et al.

[11] Patent Number: 5,580,572
[45] Date of Patent: Dec. 3, 1996

[54] STYRENE-ISOPRENE-STYRENE COPOLYMER-BASED TRANSDERMAL MATRIX SYSTEM FOR THE ADMINISTRATION OF AN OESTROGEN AND/OR A PROGESTOGEN

[75] Inventors: Claude Mikler, Dijon; Laurent Liorzou, Toulouse; Daniel Dhuique-Mayer, Dijon, all of France

[73] Assignee: Laboratoires d'Hygiene et de Dietetique, Paris, France

[21] Appl. No.: 413,216

[22] Filed: Mar. 28, 1995

[30] Foreign Application Priority Data

Mar. 28, 1994 [FR] France .................. 94 03599

[51] Int. Cl.⁶ ..................... A61F 13/00
[52] U.S. Cl. ........... 424/448; 424/449; 514/946; 514/947
[58] Field of Search .............. 424/448, 449; 514/946, 947

[56] References Cited

U.S. PATENT DOCUMENTS

| | | | |
|---|---|---|---|
| 4,299,501 | 11/1981 | Patil | 366/349 |
| 4,994,267 | 2/1991 | Sablotsky | 424/78 |
| 5,032,402 | 7/1991 | Digenis | 424/448 |
| 5,232,702 | 8/1993 | Pfister | 424/448 |

FOREIGN PATENT DOCUMENTS

| | | |
|---|---|---|
| 0156565 | 10/1985 | European Pat. Off. . |
| 0483370 | 5/1992 | European Pat. Off. . |

OTHER PUBLICATIONS

Database WPI Week 9403, Derwent Publications Ltd., London, GB; AN 94-022826 & JP-A-5 331 064 (Sekisui Chem Ind Co Ltd) Dec. 14, 1993—Abstract.

*Primary Examiner*—D. Gabrielle Phelan
*Attorney, Agent, or Firm*—Evenson, McKeown, Edwards & Lenahan, P.L.L.C.

[57] ABSTRACT

This invention is concerned with a new transdermal matrix system for the percutaneous administration of a hormone, said matrix system, which has a support and a self-adhesive matrix, comprising a matrix containing:

(a) 20 to 42 parts by weight of a poly(styrene-isoprene-styrene) triblock copolymer,
(b) 35 to 55 parts by weight of a tackifying resin.
(c) 5 to 25 parts by weight of a plasticizing agent selected from the group consisting of oleic alcohol, peglicol 5-oleate, propyleneglycol laurate or a polypropoxyl ether of cetyl alcohol,
(d) 5 to 15 parts by weight of at least one compound selected from the group consisting of:

crotamiton, and

N-substituted 2-pyrrolidones of formula I,

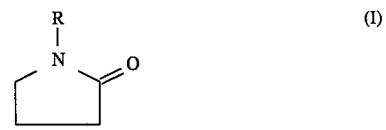

wherein R represents a $(C_1-C_{15})$-alkyl, cyclohexyl or 2-hydroxyethyl group, (e) 0,01 to 1 part by weight of a stabilizing agent and,
(f) 0,1 to 5 parts by weight of a hormone selected from the group consisting of oestrogen components, progestogen components and mixtures thereof.

It also relates to a method for prepararing said system.

No figure.

16 Claims, 3 Drawing Sheets

STYRENE-ISOPRENE-STYRENE COPOLYMER-BASED TRANSDERMAL MATRIX SYSTEM FOR THE ADMINISTRATION OF AN OESTROGEN AND/OR A PROGESTOGEN

FIELD OF THE INVENTION

The object of this invention is a new device or transdermal matrix system for the extended release of an oestrogen component and/or progestogen component, said device consisting of a support with a self-adhesive matrix which comprises a triblock copolymer with A-B-A units of poly-(styrene-isoprene-styrene) type [abbreviated to: SIS], in which said oestrogen component and/or said progestogen component is dissolved, in association with a plasticizer/promoter pair. The invention also concerns a method for preparing said matrix system.

PRIOR ART

It is known that numerous transdermal systems for the release of an oestrogen component and/or a progestogen component have already been proposed. These currently include so-called "reservoir" systems in which the active ingredient is dissolved in a solvent which serves as a transport vector towards the skin across a microporous membrane. This is the case of devices based on (i) 17-β-oestradiol and (ii) 17-β-oestradiol in association with norethisterone acetate, marketed by the company CIBA-GEIGY under the trade names ESTRADERM® TTS and ESTRAG-EST® TTS respectively.

Also, so-called matrix systems exist in which the active ingredients are dissolved or dispersed within an adhesive matrix based on polymers such as EVA, acrylic, poly(styrene-isoprene-styrene) copolymers etc.

In order to obtain a therapeutically effective end product it is essential that all these systems maintain a level of administration of the active ingredients over an extended period at sufficient rate to obtain plasma levels that are adapted to therapy requirements. Also, in order to be well accepted by the patient they must be of relatively reduced size with optimal adhesive and cohesive properties so that they are practical to use without damaging clothing through deformation of the mass of the matrix during use.

However, it is known to persons skilled in the art that oestrogen components and progestogen components are products (i) that are little soluble in the polymers used for transdermal systems, and (ii) that cross the cutaneous barrier with difficulty.

Therefore, the quantities released of these active ingredients in order to obtain the desired therapeutic effect are generally low in comparison with the initial quantities present in the transdermal devices, with the consequence that yield is low. This necessitates the use of a much higher quantity of hormone(s) than that which is actually consumed.

In this case, it is difficult to reach a compromise between an effective rate of transdermal administration of one or several hormones and appropriate physical or ergonomical properties of the systems.

Although numerous SIS triblock copolymer based formulations are known from EP-A-0 439 180, EP-A-0 285 181 or EP-A-0 483 370, none of these publications either reveals or suggests the specific formulations of the invention.

AIMS OF THE INVENTION

In the field of administration by transdermal route of an oestrogen component and/or a progestogen component, it would be desirable to have a new technical solution which uses a matrix system in which the matrix contains a SIS triblock copolymer with which the desired compromise can be reached without the above-mentioned disadvantages with, in addition, excellent yield.

According to a first aspect of the invention, it is proposed to provide a transdermal matrix system in which the matrix comprises SIS material for the administration of an oestrogen component and/or a progestogen component.

According to a second aspect of the invention, it is proposed to provide a method for the preparation of such a system.

OBJECT OF THE INVENTION

The above-mentioned purposes are achieved with a new technical solution according to which the matrix in the matrix system, which contains an oestrogen component and/or a progestogen component, is substantially made up of SIS material and a plasticizer/promoter pair.

According to the invention it is provided firstly, as a new industrial product, a transdermal matrix system for the percutaneous administration of a hormone, said matrix system which comprises a support and a self-adhesive matrix being characterized in that said matrix comprises:

(a) 20 to 42 parts by weight of a poly(styrene-isoprene-styrene) triblock copolymer, (b) 35 to 55 parts by weight of a tackifying resin.

(c) 5 to 25 parts by weight of a plasticizing agent selected from the group consisting of oleic alcohol, peglicol 5-oleate, propyleneglycol laurate or a polypropoxyl ether of cetyl alcohol, (d) 5 to 15 parts by weight of at least one compound selected from the group consisting of:
crotamiton, and
N-substituted 2-pyrrolidones of formula I,

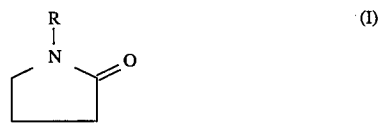

wherein R represents a $(C_1-C_{15})$-alkyl, cyclohexyl or 2-hydroxyethyl group, (e) 0,01 to 1 part by weight of a stabilizing agent and, (f) 0,1 to 5 parts by weight of a hormone selected from the group consisting of oestrogen components, progestogen components and mixtures thereof.

Secondly, a method is provided for the preparation of said transdermal matrix system, which process is characterized in that it comprises the following steps which consist either of:

(α) mixing the SIS polymer, stabilizing agent and tackifying resin at a temperature higher than 110° C., then homogenizing the resulting mixture;

(β) incorporating into the homogeneous mixture thus obtained the promoter or promoters and the plasticizer at a temperature of between 80° and 110° C., then homogenizing the resulting mixture;

(γ) incorporating into the homogeneous mixture thus obtained the hormone selected from the group consisting of oestrogen components, progestogen components and mixtures thereof, then homogenizing the resulting mixture;

(δ) coating the homogeneous mixture thus obtained, at a temperature of between 80° and 130° C. onto a temporary anti-adherent support in such manner as to obtain a coating on said support of 50 to 300 g/m²; and, (ε) transferring said coating onto a final support;

or of, (α) mixing the SIS polymer, stabilizing agent then tackifying agent in a solvent of said SIS polymer, at a temperature lower than the boiling point temperature of said solvent, then homogenizing the resulting mixture;

(β) incorporating into the mixture thus obtained the promoter or promoters and the plasticizer, then homogenizing the resulting mixture;

(γ) incorporating into the homogeneous mixture thus obtained the hormone selected from the group consisting of oestrogen components, progestogen components and mixtures thereof, then homogenizing the resulting mixture;

(δ) coating the homogeneous mixture thus obtained, at room temperature, onto a temporary anti-adherent support in such manner as to obtain a coating on said support of 50 to 300 g/m²; and, (ε) evaporating the solvent by heating said coating to a temperature higher than the boiling point temperature of said solvent, then transferring said coating onto a final support.

BRIEF DESCRIPTION OF THE DRAWINGS

In the appended drawings.

Figure 1:
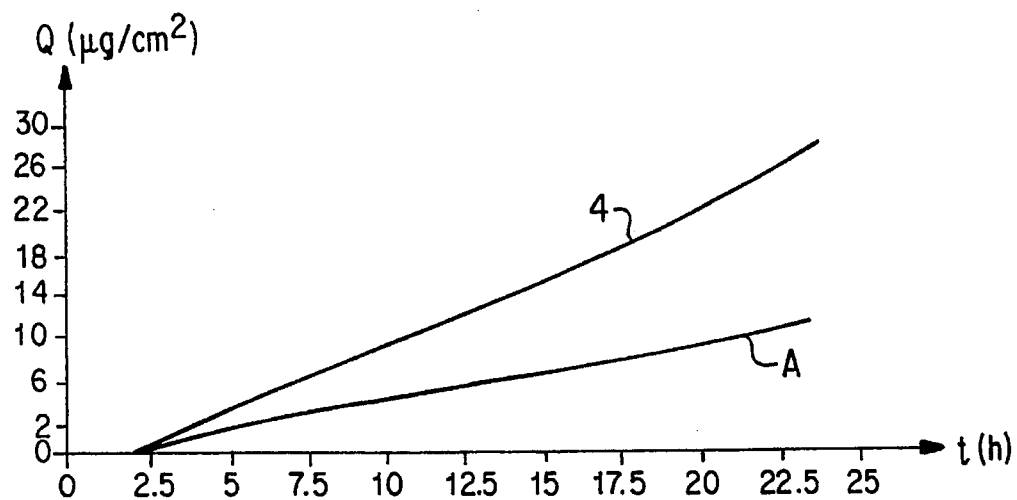
FIGS. 1 and 5 represent the quantity (Q), expressed in µg/cm², of 17-β-oestradiol released in function of time (t), expressed in hours.
Figure 2:
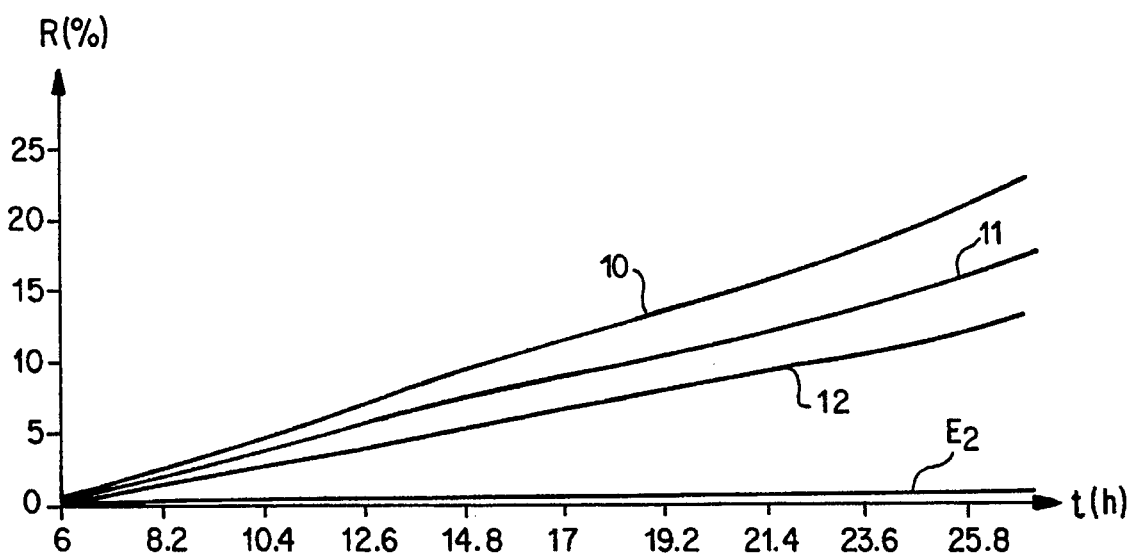
FIGS. 2–4 and 6 represent the yield (R), expressed in %, of 17-β-oestradiol or NETA (norethisterone acetate) in function of time (t), expressed in hours.
Figure 3:
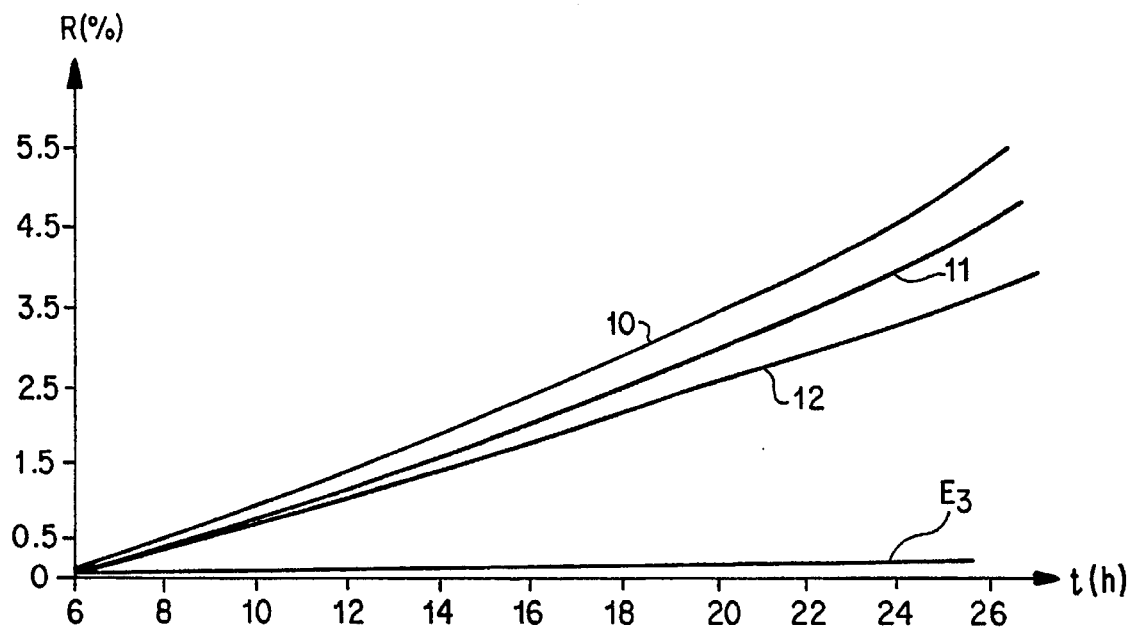
Figure 4:
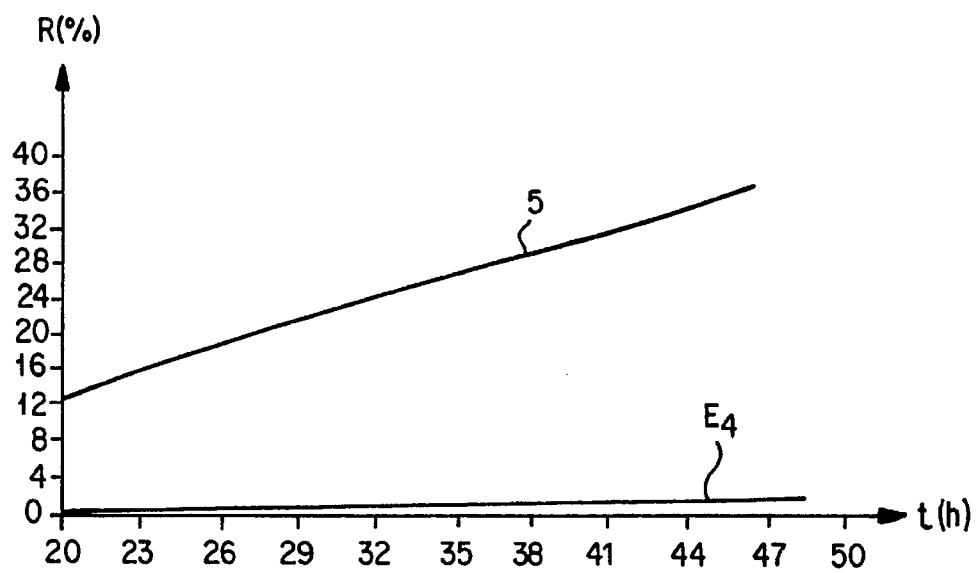
Figure 5:
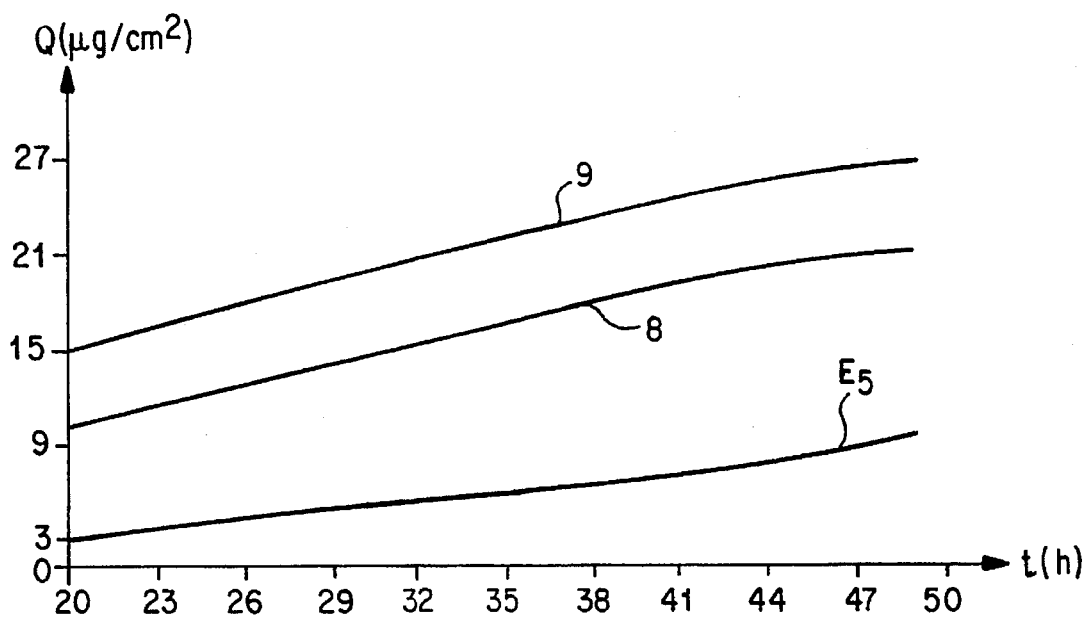
Figure 6:
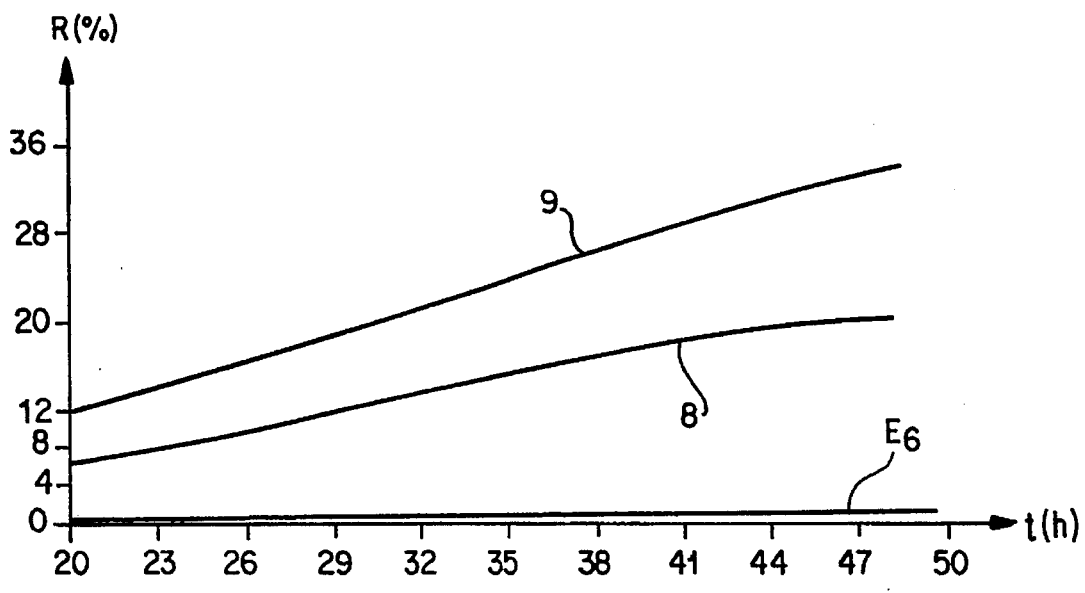

More precisely, in these drawings,

FIG. 1 gives a comparison (in the Q/t system) between curves 4 and A relating to the release of 17-β-oestradiol obtained with the product of example 4 according to the invention and the comparison product CP4;

FIG. 2 gives a comparison (in the R/t system) between curves 10, 11, 12 and E₂ relating to the yield of 17-β-oestradiol release respectively obtained with the products of examples 10, 11 and 12 according to the invention and a known transdermal product known under the tradename ESTRAGEST® marketed by the company CIBA-GEIGY;

FIG. 3 gives a comparison (in the R/t system) between curves 10, 11, 12 and E₃ relating to the yield of NETA release, respectively obtained with the products of examples 10, 11 and 12 according to the invention and said ESTRAGEST®;

FIG. 4 gives a comparison (in the R/t system) between curves 5 and E₄ relating to the yield of 17-β-oestradiol release, obtained respectively with the product of example 5 according the invention and said ESTRAGEST®;

FIG. 5 gives a comparison (in the Q/t system) between curves 8, 9 and E₅ relating to the release of 17-β-oestradiol obtained respectively with the products of examples 8 and 9 according to the invention and said ESTRAGEST®;

FIG. 6 gives a comparison (in the R/t system) between curves 8, 9, and E₆ relating to the yield of NETA release obtained respectively with the products of examples 8 and 9 according to the invention and said ESTRAGEST®.

DETAILED DESCRIPTION OF THE INVENTION

By poly(A-B-A) triblock copolymer of poly-(styrene-isoprene-styrene) type, it is meant here an SIS material with a styrene content of from 14 to 50% by weight with respect to the weight of said SIS. Preference is given to an SIS containing from 17 to 47% by weight of styrene. It is also possible to use mixtures of these SIS.

Among the tackifying resins which are suitable according the invention, mention can be made of those resins generally used by persons skilled in the art of adhesives, such as polyterpene resins or modified terpene resins, hydrogenated or polymerized rosin resins, rosin ester resins etc.

Particular preference is given to hydrocarbonated resins such as that marketed by the company EXXON CHEMICAL under the tradename ESCOREZ®-385. With these resins, used in conjunction with the preferred SIS of the invention, it is possible to obtain optimal adhesive properties.

By "active" ingredient or "hormone" is meant here any oestrogen component, any progestogen component or any oestrogen component/progestogen component mixture that can be used by transdermal route.

Among the oestrogen components that are suitable according the invention, particular mention is made of 17-β-oestradiol, and derivatives of oestradiol, notably the mono- and diesters of oestradiol, such as for example oestradiol 17-acetate, oestradiol 3.17-diacetate, oestradiol 3-benzoate, oestradiol 17-undecanoate, alkyl derivatives of oestradiol at the 17 position such as ethinyloestradiol, ethinyloestradiol 3-isopropyl-sulfonate, methyl-oestradiol, quinestrol, mestranol and, when appropriate, mixtures thereof.

Among the progestogen components which are suitable according to the invention, particular mention is made of progesterone, medrogesterone and their derivatives (especially 17-hydroxyprogesterone acetate, medroxyprogesterone acetate), norethisterone and its derivatives especially 17-norethisterone acetate.

According to the present invention the use of 17-β-oestradiol for the oestrogen component and of norethisterone (NETA) for the progestogen component is preferred. According to an embodiment variant, the transdermal matrix system according to the invention can contain an oestrogen component and a progestogen component simultaneously.

Among the stabilizing agents used according to the invention, mention can be made of the antioxidant agents widely used by persons skilled in the art, for example the products marketed by the company CIBA-GEIGY under the tradename IRGANOX® 565 or IRGANOX® B215.

The promoter, product (d), can be selected from the group consisting of crotamiton, N-alkyl-2-pyrrolidone compounds, in which the alkyl group is a $C_1-C_{15}$ one, N-(2-hydroxyethyl)-2-pyrrolidone, N-cyclohexyl-2-pyrrolidone and mixtures thereof.

Among the N-($C_1-C_{15}$)-alkyl-2-pyrrolidones used in the present invention, preference is given to N-methyl-2-pyrrolidone, N-ethyl-2-pyrrolidone, N-octyl-2-pyrrolidone, N-dodecyl-2-pyrrolidone, marketed by the company GAF CORPORATION under the respective tradenames of NMP®, NEP®, SURFADONE®LP 100 and SURFADONE®LP 300, and mixtures thereof.

When the plasticizer is a polypropoxyl ether of cetyl alcohol, preference is given to a compound containing in particular 10 moles of propylene oxide per one mole of cetyl alcohol, such as for example the product marketed by the company CRODA FRANCE S.A. under the tradename PROCETYL®10.

The support receiving the matrix may be any support that is generally used for transdermal systems whether occlusive or not, of variable thickness which is impervious to the constituents of the matrix. Preference can be given for example to a support in polyethylene, polypropylene or polyester film, a complex (or composite) consisting of polyethylene and a copolymer of vinyl acetate and ethylene, or even foams.

For practical purposes, the surface of the matrix, which is not attached to the support, may be covered by a protective layer or film which can be peeled off before using the device; said apparatus can itself be packed in a sealed protection, such as for example polyethylene-aluminium complexes.

Owing to the specificity of the composition of those formulations that can form the matrix, only the matrix system according to the invention offers the numerous advantages that are described hereunder.

It was found that only the composition defined hereabove containing (1) a plasticizer/promoter pair, in which (i) the plasticizing agent represents oleic alcohol, peglicol 5-oleate, propyleneglycol laurate or a polypropoxyl ether of cetyl alcohol, and (ii) the promoter is at least one compound selected from the N-substituted 2-pyrrolidones of formula I and crotamiton, and (2) an SIS material, allows the achievement both of remarkable yield and the desired adhesive and cohesive properties.

Identical results cannot be obtained with a matrix with another type of copolymer base such as for example a copolymer of ethylene and vinyl acetate (EVA) used in conjunction with this plasticizer/promoter pair.

This can no doubt be attributed to (i) a particular synergic effect between the nature of the poly(styrene-isoprene-styrene) triblock copolymers which have a propensity to "repel" the hormone or hormones present, which are insoluble in the latter, and (ii) to the role played by specific plasticizing agents which widen the SIS polymeric chains giving them wider movement thereby reducing the rigidity of the macromolecular network, which facilitates the circulation of the hormone or hormones.

These placticizers, however, which are derived from fatty substances may, if they are used in too great quantity, deteriorate the adhesive and/or cohesive properties of the matrix. It is therefore essential that they be used in conjunction with one or several promoters of cutaneous permeation of a different nature such as crotamiton or N-substituted 2-pyrrolidones of formula I in order to obtain the desired administration rates and to attain better yield without loss of adhesion or cohesion.

Said crotamiton and N-substituted 2-pyrrolidones of formula I also allow improved solubility of the hormones used in the matrix.

These specific formulations lead to self-adhesive transdermal systems with good cohesive and adhesive properties and providing yields of the oestrogen component at 24 hours or 48 hours in the region of 10 to 84% and of the progestogen component in the region of 3.5 to 32%.

The possibility of using less oestrogen component and/or progestogen component while obtaining greater administered quantities simplifies the development and production of formulations forming the matrix of the devices.

In this way the problems of hormone solubility in SIS copolymers as well as the risks of physical incompatibility with other constituents of the matrix can be reduced or eliminated. This also applies to crystallization problems with the hormones and instability problems of the devices in the course of time, such phenomena being unacceptable for the approval and marketing of products intended for therapeutical purposes such as transdermal systems.

A last but non-negligible advantage is related to cost price which is substantially reduced compared with known devices of the prior art, owing to the use of a low quantity of hormone whose price is high.

The transdermal matrix systems according to the invention are produced using the techniques generally used by persons skilled in the art: either by coating (in solvent phase), or using the so-called "hot-melt" technique (that is to say without the presence of a solvent).

In either case, for industrial production purposes, large surface areas are coated and then cut to obtain devices whose size, according to the quantity of hormone(s) present per unit surface area, is adapted to the chosen dose of active ingredient to be administered over a given time.

For the so-called in solvent phase technique, a method is provided for the preparation of a self-adhesive transdermal matrix system according to the invention which comprises the following steps:

(1) into a thermostat-fitted reactor containing a solvent of the polymer, heated to a temperature that is lower than the boiling point temperature of the solvent (for example 60° C. for ethyl acetate), are added the SIS copolymer, the stabilizer and then the tackifying resin, under stirring until the mixture is fully homogenized;

(2) under continued stirring and heating to the same temperature all the liquid compounds are incorporated, that is to say the promoter or promoters and the plasticizer, the resulting mixture being homogenized;

(3) the active ingredient or ingredients, either directly in powder form or in a solution in a solvent of the oestrogen component and/or progestogen component such as for example tetrahydrofuran, are incorporated into the mixture obtained at step (2), under continued stirring and heating to the same temperature until complete homogenization;

(4) the homogeneous mixture obtained at step (3) is applied onto a non-adherent temporary support, for example a silicone polyester film, in order to obtain a deposit of 50 to 300 g/m$^2$;

(5) the deposit thus obtained is heated to evaporate the solvent at a temperature, depending upon the boiling point of the solvent, of between 40° and 110° C., preferably at a temperature between 60° and 80° C.; and, (6) the resulting dry matrix is transferred to the chosen final support.

For the "hot-melt" technique a process is provided which comprises the following steps:

(1a) in a mixer at a temperature above 110° C., preferably a temperature of 130° C., the tackifying resin is incorporated into the SIS polymer/stabilizer in successive portions of 10%, 30% and 60% while stirring, in such manner that after each portion is added a perfectly homogeneous mixture is obtained;

(2a) to the mixture obtained at step(1a) the most liquid products of the formulation are gradually incorporated, that is to say the plasticizer and the promoter or promoters under continued stirring and at temperatures that are generally lower than for step (a) as determined by the thermal stability of the products; stirring is continued until complete homogenization of the resulting mixture;

(3a) the active ingredient or ingredients are incorporated into the homogeneous mixture obtained at step (2a) at a temperature of about 100° C., and stirring is continued until a perfectly homogeneous mixture is obtained;

(4a) the homogeneous mixture thus obtained is applied, at a temperature of between 80° and 130° C., to a temporary non-adherent support, in particular a silicone polyester film, in order to obtain a deposit of 50 to 300 $g/m^2$; and, (5a) the matrix obtained at step (4a) is transferred to the chosen final support.

The transdermal systems according to the invention are particularly useful for the treatment of menopause symptoms and resulting cardio-vascular risks, osteoporosis and any therapy which uses the percutaneous route requiring the administration of oestrogens and/or progestogens.

BEST MODE

The best mode of the invention consists in using a transdermal matrix system whose matrix contains, per total 100 parts by weight:

(a) 37.3 parts by weight of poly(styrene-isoprene-styrene) triblock copolymer, (b) 38 parts by weight of tackifying resin, (c) 15 parts by weight of propylene glycol laurate, (d) 7 parts by weight of N-octyl-2-pyrrolidone, (e) 0.2 part by weight of a stabilizing agent, (f) 0,5 part by weight of 17-β-oestradiol, and (g) 2 parts by weight of norethisterone acetate, Other advantages and characteristics of the invention will be better understood on reading the following description of working examples and comparative assays.

These examples and assays are evidently by no means restrictive but are given by way of illustration.

For practical purposes hereunder, abbreviations have been used:

NETA: norethisterone acetate
SIS: poly(styrene-isoprene-styrene) triblock copolymer
EVA: ethylene/vinyl acetate copolymer.

EXAMPLE 1

In a 250 ml beaker are added 13.9 g of VECTOR® 4211D (SIS copolymer marketed by the company EXXON CHEMICAL), 23 g of ECR® 385 (tackifying resin marketed by the company EXXON CHEMICAL), 9 g of PROCETYL® 10 (polypropoxyl ether of cetyl alcohol marketed by CRODA FRANCE SA), 3 g of SURFADONE® LP 100 (N-octyl-2-pyrrolidone, marketed by the company GAF CORPORATION), 0.1 g of IRGANOX®565 (antioxidant marketed by the company CIBA-GEIGY) and 19.65 g of ethyl acetate. The mixture is stirred under heating to 60° C. until complete dissolution of the compounds. A solution of 1 g of NETA is then added previously dissolved in 5 g of tetrahydrofuran. The mixture thus obtained is stirred for approximately 30 minutes until complete homogenization. It is left to cool and degas until the bubbles have completely disappeared. The resulting mass is applied to a silicone polyester film to obtain a deposit of (110±10) $g/m^2$, at room temperature (15°–20° C.). The coating thus achieved is heated to 50° C. for at least 30 minutes and then transferred to a non-silicone polyethylene support. It is then cut to appropriate size and packed in sachets.

A system is obtained in which the initial quantity of NETA is 231 $\mu g/cm^2$.

EXAMPLE 2

Procedure is identical to example 1 but using 13.4 g of VECTOR® 4211D, 0.1 g of IRGANOX® 565, 26.5 g of ECR® 385, 5 g of oleic alcohol, 4.5 g of crotamiton [N-ethyl-N(2-methylphenyl)-2-butenamide, marketed by the company BOEHRINGER INGELHEIM], 20 g of ethyl acetate and 0.5 g of 17-β-oestradiol dissolved in 2.5 g de tetrahydrofuran. Coating is carried out to obtain a deposit of (100±10) $g/m^2$.

A system is obtained in which the initial quantity of 17-β-oestradiol is 94.5 $\mu g/cm^2$.

EXAMPLE 3

Procedure is identical to example 1 but using 13.9 g of VECTOR® 4211D, 0.1 g of IRGANOX® 565, 27.5 g of ECR® 385, 5 g of oleic alcohol, 3 g of SURFADONE® LP 300, 20.8 g of ethyl acetate and 0.5 g of 17-β-oestradiol dissolved in 2.5 g of tetrahydrofuran. Coating is carried out to obtain a deposit of (100±10) $g/m^2$.

A system is obtained in which the initial quantity of 17-β-oestradiol is 91 $\mu g/cm^2$.

EXAMPLE 4

Procedure is identical to example 1 but using 7.25 g of VECTOR® 4211D, 0.07 g of IRGANOX® 565, 11 g of ECR® 385, 3.75 g of LABRAFIL® 1944Cs (peglicol 5-oleate marketed by the company GATTEFOSSE), 2.5 g of crotamiton, 10 g of ethyl acetate and 0.5 g of 17-β-oestradiol dissolved in 2.5 g of tetrahydrofuran. Coating is carried out to obtain a deposit of (90±10) $g/m^2$.

A system is obtained in which the initial quantity of 17-α-oestradiol is 181.7 $\mu g/cm^2$.

EXAMPLE 5

Procedure is similar to example 4 but using 12.9 g of VECTOR® 4211D, 0.1 g of IRGANOX®565, 26 g of ECR® 385, 8 g of LABRAFIL® 1944Cs, 2.5 g of SURFADONE® LP 300, 19.4 g of ethyl acetate and 0.5 g of 17-g-oestradiol dissolved in 2.5 g of tetrahydrofuran. Coating is carried out to obtain a deposit of (100±10) $g/m^2$.

A system is obtained in which the initial quantity of 17-β-oestradiol is 87.1 $\mu g/cm^2$.

EXAMPLE 6

Procedure is similar to example 2 but using 13.16 g of VECTOR® 4211D, 0.1 g of IRGANOX® 565, 26.5 g of ECR® 385, 5.08 g of oleic alcohol, 4.53 g of crotamiton, 19.8 g of ethyl acetate and 0.75 g of 17-β-oestradiol dissolved in 3.75 g of tetrahydrofuran. Coating is carried out to obtain a deposit of (100±10) $g/m^2$.

A system is obtained in which the initial quantity of 17-β-oestradiol is 159 $\mu g/cm^2$.

EXAMPLE 7

Procedure is similar to example 3 but using 0.75 g of 17-β-oestradiol dissolved in 3.75 g of tetrahydrofuran, 13.64 g of VECTOR® 4211D, 0.1 g of IRGANOX® 565, 27.51 g of ECR® 385, 5 g of oleic alcohol, 3 g of SURFADONE® LP 300 and 20.5 g of ethyl acetate. Coating is carried out to obtain a deposit of (100±10) g/m².

A system is obtained in which the initial quantity of 17-β-oestradiol is 162.3 µg/cm².

EXAMPLE 8

Procedure is similar to example 1 but using 13.9 g of VECTOR® 4211D, 0.1 g of IRGANOX® 565, 24 g of ECR® 385, 3.5 g of SURFADONE® LP 300, 7.5 g of LAUROGLYCOL® (mixture of mono and di-ester of propyleneglycol and lauric acid marketed by the company GATTEFOSSE) instead of PROCETYL® 10, 19.9 g of ethyl acetate, 0.25 g of 17-β-oestradiol and 0.75 g of NETA dissolved in 5 g of tetrahydrofuran. Coating is carried out to obtain a deposit of (100±10) g/m².

A system is obtained in which the initial quantity of 17-β-oestradiol is 48.6 g/cm² and the initial quantity of NETA is 145.3 µg/cm².

EXAMPLE 9

Procedure is identical to example 8 but using 15.9 g of VECTOR® 4211D, 0.1 g of IRGANOX® 565, 21 g of ECR® 385, 7.5 g of LAUROGLYCOL®, 4.5 g of crotamiton (in replacement of SURFADONE® LP 300), 21.15 g of ethyl acetate, 0.25 g of 17-β-oestradiol and 0.75 g of NETA dissolved in 5 g of tetrahydrofuran. Coating is carried out to obtain a deposit of (70±10) g/m².

A system is obtained in which the initial quantity of 17-β-oestradiol is 33.1 µg/cm² and the initial quantity of NETA is 99.4 µg/cm².

EXAMPLE 10

Procedure is identical to example 1 but using 14.9 g of VECTOR® 4211D, 0.11 g of IRGANOX® 565, 23.25 g of ECR® 385, 7 g of PROCETYL® 10, 3.56 g of SURFADONE® LP 100, 20.7 g of ethyl acetate, 0.25 g of 17-β-oestradiol and 1 g of NETA dissolved in 6.25 g of tetrahydrofuran. Coating is carried out to obtain a deposit of (100±10) g/m².

A system is obtained in which the initial quantity of 17-β-oestradiol is 51 µg/cm² and the initial quantity of NETA is 207.1 µg/cm².

EXAMPLE 11

Procedure is identical to example 10 but SURFADONE® LP 100 is replaced by 3.5 g of SURFADONE® LP 300. Coating is carried out to obtain a deposit of (120±10) g/m².

A system is obtained in which the initial quantity of 17-β-oestradiol is 60.5 µg/cm² and the initial quantity of NETA is 242 µg/cm².

EXAMPLE 12

Procedure is identical to example 10 but using 14.65 g of VECTOR® 4211D, 0.1 g of IRGANOX® 565, 21.75 g of ECR® 385, 7 g of PROCETYL® 10, 5 g of crotamiton, 20.1 g of ethyl acetate, 0.25 g of 17-β-oestradiol and 1 g of NETA dissolved in 6.25 g de tetrahydrofuran. Coating is carded out to obtain a deposit of (120±10) g/m².

A system is obtained in which the initial quantity of 17-β-oestradiol is 60.5 µg/cm² and the initial quantity of NETA is 235.4 µg/cm².

EXAMPLE 13

Procedure is similar to example 8 but using 18.65 g of VECTOR® 4211D, 0.1 g of IRGANOX® 565, 19 g of ECR® 385, 3.5 g de SURFADONE® LP 100, 7.5 g of LAUROGLYCOL®, 23 g of ethyl acetate dissolved in 5 g of tetrahydrofuran, 0.25 g of 17-β-oestradiol and 0.75 g of NETA. Coating is carried out to obtain a deposit of (100±10) g/m².

A system is obtained in which the initial quantity of 17-β-oestradiol is 47.3 µg/cm², and the initial quantity of NETA is 190 µg/cm².

For the purpose of comparison the following EVA-based matrices were made.

COMPARISON PRODUCT CP1

In a 250 ml beaker, 29 g of LEVAPREN® 450P (EVA marketed by the company BAYER), 15.5 g of PROCETYL® 10, 3.5 g of SURFADONE® LP 100 and 67.7 g of ethyl acetate are added. They are heated to 60° C. under stirring for 5 hours until complete dissolution of the EVA.

2 g of NETA previously dissolved in 10 g of tetrahydrofuran are then added. The mixture thus obtained is stirred while heating for approximately 30 minutes until complete homogenization. The mixture thus obtained is left to cool and degas until complete elimination of bubbles. The resulting mass is applied at room temperature onto silicone paper to a thickness of (120±10) g/m². The coating thus made is heated to 70° C. for at least 30 minutes, then transferred to a final support in non-silicone polyethylene. It is then cut to appropriate sizes and packed in sachets.

A system is obtained in which the initial quantity of NETA is 488 µg/cm².

COMPARISON PRODUCT CP2

Procedure is similar to CP1, but using instead 29 g of LEVAPREN® 450P, 16.5 of oleic alcohol, 3.5 g of crotamiton, 67.6 g of ethyl acetate and 1 g of 17-β-oestradiol dissolved in 5 g of tetrahydrofuran. Coating is carded out to obtain a deposit of (80±10) g/m².

A system is obtained in which the initial quantity of 17-β-oestradiol is 157 µg/cm².

COMPARISON PRODUCT CP3

Procedure is similar to CP2, but using 1 g of 17-β-oestradiol dissolved in 5 g of tetrahydrofuran, 29 g of LEVAPREN® 450P, 16.25 g of oleic alcohol, 67.6 g of ethyl acetate and 3.75 g of SURFADONE® LP 300. Coating is carried out to obtain a deposit of (80±10) g/m².

A system is obtained in which the initial quantity of 17-β-oestradiol is 169.6 µg/cm².

COMPARISON PRODUCT CP4

An EVA-based formulation used here is of the same type as those described in published document FR-A-2 612 783 mentioned above.

In a beaker, 21.97 g of LEVAPREN® 450P is added to 12.54 g of EUTANOL® G (2-octyl-dodecanol, marketed by the company HENKEL). The mixture is heated to 130° C. and stirred and to it is added 6.03 g of ETHOCEL® 20 (ethylcellulose marketed by the company DOW CHEMICAL) and then 6.46 of EUTANOL® G. Stirring is continued until a homogenous non-granular mixture is obtained which is then left to cool. The mass is then heated to 80° C. and to it is added a solution of 1.5 g of 17-β-oestradiol previously dissolved at 70° C. in 12 g of anhydrous ethanol. The mass and solution are mixed for at least one hour until complete homogenization. The mass thus obtained is applied to a silicon paper support at a temperature of 70° C. in order to obtain a deposit to a thickness of $(150\pm10)$ g/m$^2$. Drying is carried out at 80° C. to evaporate the ethanol, and the matrix thus obtained is transferred to a final polyethylene support. It is cut to appropriate sizes which are packed in sachets.

A system in obtained in which the initial quantity of 17-β-oestradiol is 463.6 µg/cm$^2$.

ASSAYS

Certain results obtained from comparative assays have been regrouped in FIGS. 1 to 6.

Using the devices described in the examples given above ex vivo measurements were made of the quantities of hormone or hormones released over 24 hours or 48 hours on various skin models and the related yields were calculated. The comparison with other already known systems clearly illustrates the advantages of the devices as claimed in the invention.

For this purpose ex vivo permeation tests were made on the abdominal skin of male "nude" mice in accordance with the following protocol.

The quantities of hormones released by a transdermal device with a surface area of 2.54 cm$^2$ previously stamped out and placed on a 3.14 cm$^2$ disk of abdominal skin of male "nude" mice are measured using a glass static cell with a thermostat setting of 37° C. and containing a receptor compartment with a volume of 11.5 ml having, as a receptive phase, a physiological saline solution/PEG$_{400}$ (75/25) V/V mixture.

Samples were taken in the receptor solutions at 2, 4, 6, 8, 12, 16, 20 and 24 hours that were titrated by liquid chromatography.

Given the variability of results related to the intrinsic permeability of skin samples, each permeation test per sample of transdermal device was carried out on a minimum number of 3 to 5 skin samples.

A result is given, which is the average for each device, that was obtained with these tests.

The ratio between this average value of the quantities of hormone(s) released after 24 hour kinetics and the initial quantity of hormone(s) contained in the apparatus, can be used to evaluate the yield in 24 hours of the transdermal systems according to the invention.

The results obtained are given in Table 1.

The quantities released in 24 hours were also calculated in comparison with the devices described in the prior art. Using the same protocol as previously, ex vivo cutaneous permeation tests on the abdominal skin of "nude" male mice were made with different devices according to the invention containing 17-β-oestradiol and with a self-adhesive matrix system (comparison product CP4) of the same type as those described in FR-A-2 612 785.

The quantities released at 24 hours and the calculated yields are given in Table II.

Finally, comparative measurements were made in relation to the only known system which is currently marketed and which contains both an oestrogen and a progestogen, namely the product ESTRAGEST® marketed by the company CIBA-GEIGY. This product is also the only product currently available on the market which contains a progestogen although the latter is combined with 17-β-oestradiol. The same protocol as previously was followed to carry out ex vivo cutaneous permeation tests on the abdominal skin of male "nude" mice. The quantities released in 24 hours were again measured and the yields were calculated using the same principle.

With regard to the product ESTRAGEST®, the device consists of two reservoirs joined side by side containing a total of 10 mg of 17-β-oestradiol and 30 mg of NETA, each reservoir containing a mixture of 5 mg of 17-β-oestradiol and 15 mg of NETA.

Cutaneous permeation measurements were made following the same protocol on only one of the two reservoirs placed on a skin sample of 3.14 cm$^2$.

The initial quantities of each hormone contained in this reservoir were reduced to the initial quantity of said hormone per unit surface area expressed in µg/cm$^2$.

In one reservoir the average initial hormone value per unit surface area was $(1590\pm30)$ µg/cm$^2$ for 17-β-oestradiol and $(4770\pm30)$ µg/cm$^2$ for NETA.

Also, the ratio between respectively (i) the average value of 17-β-oestradiol or NETA released in 24 hours and (ii) the initial quantities contained in the reservoir can be used to calculate the yields in 24 hours of 17-β-oestradiol and NETA.

As a first step, a comparison was made between matrix systems as claimed in the invention containing 17-β-oestradiol and NETA, and the previously mentioned known transdermal system ESTRAGEST®. The results obtained were entered into Table III below.

As a second step, ex vivo comparative measurements were also made on another skin model, swine-ear skin, which generally gives ex vivo results closer to those obtained with ex vivo permeation test measurements on human skin.

The procedure used for these measurements was identical to that used for ex vivo measurements on the abdominal skin of "nude" mice. This time the disk measuring 3.14 cm$^2$ was of swine-ear skin. The receptive phase remained a mixture of physiological saline solution/PEG$_{400}$ (75/25) V/V. However this time samples were taken over 48 hours.

The result obtained was also the average obtained for each device tested on a minimum number of 3 to 5 skin samples.

The ratio between (i) this average value and the quantity of hormones released after 48 hour kinetics and (ii) the initial quantity of hormone contained in the device was used to calculate the yield in 48 hours of the transdermal systems.

The related results were entered into Tables IV and V below.

With respect to the study made for Table I the quantities released in 24 hours were determined between 2 matrix systems whose matrix comprises the same plasticizer/promoter pair but a copolymer of a different nature. For examples 1 to 3 a SIS was used and for examples CP1 to CP3 an EVA was used.

Analysis of Table I shows that with regard to NETA, when comparing the product of example 1 with CP1, yields are 2.5 times higher for SIS compared to EVA with the same plasticizer/promoter pair, namely the pair PROCETYL® 10/SURFADONE® LP 100. Also the quantity of NETA released was higher for the product of example 1.

Similar results were obtained with 17-β-oestradiol when comparing the product of example 2 with CP2 in which the plasticizer/promoter couple is the oleic alcohol/crotamiton pair. In this case the yield was also higher with SIS being 1.7 times higher.

In the same way if the results obtained are analysed by comparing the product of example 3 with CP3 in which the pair oleic alcohol//SURFADONE® LP 300 was used, the yield obtained for 17-β-oestradiol was 4 times higher with the SIS (example 3) compared with the EVA (CP3). In this case the release of 17-β-oestradiol was 2.2 times higher. The SIS therefore provides a transdermal matrix system which gives better release than with the EVA even though it was used in conjunction with the same plasticizer/promoter pair.

All the results in Table I therefore show that the yields for the devices according to the invention are better owing to the specific combination of the SIS material and a plasticizer/promoter pair according to the invention, and that the quantities released are the same or higher.

In respect of the study made for Table II the devices according to the invention were compared with a device that was identical to those described in FR-A-2 612 785.

The analysis of this table shows that in all cases the quantities of 17-β-oestradiol released were higher than with the CP4 device according to the FR-A-2-612 785. This result is perfectly illustrated by FIG. 1 which compares the products of example 4 and CP4.

With regard to yields, it was observed, in comparison with the CP4 device that:

yield was 7 times higher with example 2, yield was 13 times higher with example 3, yield was 7 times higher with example 6, yield was 10 times higher with example 7, yield was 6 times higher with example 4.

To conclude, in all cases, whichever plasticizer/promoter pair was used, oleic alcohol/crotamiton for the products in examples 2 and 6, oleic alcohol/SURFADONE® LP 300 for the products in examples 3 and 7, or LABRAFIL® 1944 Cs/crotamiton for the product in example 4, yields were always higher (in the order of 6 to 13 times) than with CP4.

The quantities released were nearly always approximately 2.5 times higher than with the corresponding EVA matrix.

For the study made in respect of Table III, the matrix systems as claimed in the invention containing the two hormones: 17-β-oestradiol and NETA were compared with the product ESTRAGEST®. The results in Table III show that in all cases (i) the quantities of 17-β-oestradiol released in 24 hours were approximately between 2 and 3 times higher than with the ESTRAGEST® product and (ii) the quantities of NETA released in 24 hours were equivalent or higher than those with the comparative product ESTRAGEST®.

Also, yields both for 17-β-oestradiol and for NETA were always very much higher than those with the ESTRAGEST® system. More specifically it was observed that compared with the latter the data for 17-β-oestradiol respectively show:

a yield 90 times higher for example 10, a yield 72 times higher for example 11, a yield 47 times higher for example 12, and for NETA, respectively:

a yield 25 times higher for example 10, a yield 20 times higher for example 11, a yield 19 times higher for example 12, These very considerable differences provide evidence of the advantages of the transdermal systems according to the invention in relation to the only combined transdermal system currently marketed.

These differences are corroborated by FIGS. 2 and 3 which represent the yield in % of 17-β-oestradiol in terms of time (curve 11) and the yield in % of NETA in terms of time (curve 12).

It is also observed that in this case, whichever promoter was used in conjunction with the plasticizer (in this case PROCETYL® 10) results with crotamiton or an N-alkyl-2-pyrrolidone (SURFADONE® LP 300 or SURFADONE® LP 100) were always remarkable.

In respect of the studies made with swine-ear skin (tables IV and V) the device according to the invention were compared with the product ESTRAGEST®.

Table IV relating to the release and yield of 17-β-oestradiol shows that with this skin model the quantity of 17-β-oestradiol released in 48 hours and the yield was much higher with the product of example 5 according to the invention than with the ESTRAGEST® device. The quantity released was 3 times higher than with the ESTRAGEST® product.

FIG. 4 which represents the yield (%) of 17-β-oestradiol in terms of time for the product of example 5 and for said ESTRAGEST® also illustrates this result.

The result of table IV shows that, compared with the ESTRAGEST® device, example 5 has a yield that is 57 times higher.

These similarly high values for this new swine-ear skin model therefore confirm the results already obtained with ex vivo cutaneous permeation tests on the abdominal skin of mice.

The results obtained further demonstrate the advantages of the plasticizer/promoter pair in which the plasticizer is peglicol oleate (LABRAFIL 1944,Cs) and the promoter is SURFADONE® LP 300, with the SIS.

In table V a comparison is made, on swine-ear skin, between the devices comprising both hormones, 17-β-oestradiol and NETA, according to the invention (products of examples 8, 9 and 13) and the product ESTRAGEST®.

On this skin model with a transdermal matrix system according to the invention, the yields for 17-β-oestradiol were found to be much higher than those of the ESTRAGEST® apparatus.

FIG. 5 also illustrates the same phenomenon regarding the quantities of 17-β-oestradiol released in 48 hours.

Table V shows, in particular, that compared with the product ESTRAGEST®, yields were respectively 138 times higher for the product of example 9, 72 times higher for the product of example 8 and 107 times higher for the product of example 13.

Also, with regard to NETA on this skin model, much higher yields were observed than with the ESTRAGEST® apparatus.

This is perfectly illustrated by FIG. 6 which represents the yield (%) in terms of time, even if the phenomenon is less marked than with 17-β-oestradiol, as it is known that NETA has more difficulty crossing the cutaneous barrier.

The results of table V show that, compared with the ESTRAGEST® apparatus, the yield was 21 times higher for the product of example 8, the yield was 35 times higher for the product of example 9 and the yield was 25 times higher for the product of example 13.

If, in the plasticizer/promoter pair, the plasticizer is represented by LAUROGLYCOL® and the promoter by crotamiton (example 9) or an N-alkyl-2-pyrrolidone (SURFADONE® LP 300 for example 8 SURFADONE®LP 100 for example 13) their association with an SIS material again allows the achievement of remarkable results.

To conclude, all the results given above demonstrate the undeniable advantages of the transdermal matrix system according to the invention on different skin models with in vivo tests compared with the only product marketed that contains an oestrogen and a progestogen and with other self-adhesive matrix devices described in the prior art.

In particular the results show that in conjunction with an SIS copolymer the plasticizer/promoter pairs of the invention allow the achievement of higher yields that are exceptional in certain cases.

TABLE I

|  | Ex 1 NETA | CP1 NETA | Ex 2 Es | CP2 Es | Ex 3 Es | CP3 Es |
|---|---|---|---|---|---|---|
| $Q_0$ | 231 | 488 | 94,5 | 157 | 91 | 169,6 |
| $Q_{24}$ | 12.7 ± 3 | 10 ± 1,5 | 16.4 ± 1,8 | 15.8 ± 5 | 29 ± 3.2 | 13.4 ± 2 |
| R | 5.5 | 2.05 | 17.3 | 10 | 32 | 7.9 |

$Q_0$: initial quantity of 17-β-oestradiol or NETA expressed in µg/cm$^2$
$Q_{24}$: quantity of 17-β-oestradiol or NETA released in 24 hours expressed in µg/cm$^2$
R: yield expressed as a percentage (R = 100.$Q_{24}$/$Q_0$)

TABLE II

|  | Ex 2 | Ex 3 | Ex 4 | Ex 6 | Ex 7 | CP4 |
|---|---|---|---|---|---|---|
| $Q_0$ | 94.5 | 91 | 181.7 | 159 | 162.3 | 463.6 |
| $Q_{24}$ | 16.4 ± 1,8 | 29 ± 3.2 | 26.1 ± 1,5 | 27 ± 1.3 | 42.2 ± 3.7 | 11.22 ± 1 |
| R | 17.3 | 32 | 14.4 | 17 | 26 | 2.42 |

$Q_0$: initial quantity of 17-β-oestradiol expressed in µg/cm$^2$
$Q_{24}$: quantity of 17-β-oestradiol released in 24 hours expressed in µg/cm$^2$
R: yield expressed as a percentage, that is 100.$Q_{24}$/$Q_0$

TABLE III

|  |  | Ex 10 | Ex 11 | Ex 12 | ESTRAGEST ® |
|---|---|---|---|---|---|
| Es | $Q_0$ | 51 | 60.5 | 60.5 | 1565 |
|  | $Q_{24}$ | 8.95 ± 0.9 | 8.74 ± 0.16 | 5.76 ± 0.6 | 3.13 ± 0.21 |
|  | R | 17.56 | 14.4 | 9.52 | 0.2 |
| NETA | $Q_0$ | 207.1 | 242 | 235.4 | 4820 |
|  | $Q_{24}$ | 9.05 ± 1.4 | 10.11 ± 0.6 | 7.65 ± 0.4 | 8.2 ± 1 |
|  | R | 4.37 | 4.18 | 3.25 | 0.17 |

Es: 17-β-oestradiol
NETA: norethisterone acetate
$Q_0$: initial quantity of Es or NETA expressed in µg/cm$^2$
$Q_{24}$: quantity of Es or NETA released at 24 hours expressed in µg/cm$^2$
R: yield expressed as a percentage, that is 100.$Q_{24}$/$Q_0$

TABLE IV

|  | Ex 5 | ESTRAGEST ® |
|---|---|---|
| $Q_0$ | 87.1 | 1584 |
| $Q_{48}$ | 30.5 ± 7 | 9.66 ± 0.9 |
| R | 35 | 0.61 |

$Q_0$: initial quantity of 17-β-oestradiol expressed in mg/cm$^2$
$Q_{48}$: quantity of 17-β-oestradiol released in 48 hours expressed in mg/cm$^2$
R: Yield expressed as a percentage, that is 100.$Q_{24}$/$Q_0$

TABLE V

|  |  | Ex 8 | Ex 9 | Ex 13 | ESTRAGEST ® |
|---|---|---|---|---|---|
| Es | $Q_0$ | 48.6 | 33.4 | 47.3 | 1584 |
|  | $Q_{48}$ | 21.4 ± 2 | 27.8 ± 3 | 12 ± 2 | 9.66 ± 0.9 |
|  | R | 44 | 84 | 65 | 0.61 |
| NETA | $Q_0$ | 145.3 | 99.4 | 190 | 4740 |
|  | $Q_{48}$ | 27.6 ± 7 | 31.7 ± 8 | 41.8 | 42.6 ± 7 |
|  | R | 19 | 31.9 | 22 | 0.9 |

$Q_0$: initial quantity of Es or NETA expressed in µg/cm$^2$
$Q_{48}$: quantity of Es or NETA released in 48 hours expressed in µg/cm$^2$
R: yield expressed as a percentage, that is 100 · $Q_{24}$/$Q_0$

What is claimed is:

1. A self-adhesive transdermal matrix system for the administration of a hormone by percutaneous route, said matrix system, which has a support and a self-adhesive matrix, comprises a matrix consisting essentially of:
   (a) 20 to 42 parts by weight of a poly(styrene-isoprene-styrene) triblock copolymer,
   (b) 35 to 55 parts by weight of a tackifying resin.
   (c) 5 to 25 parts by weight of a plasticizing agent selected from the group consisting of oleic alcohol, peglicol 5-oleate, propyleneglycol laurate or a polypropoxyl ether of cetyl alcohol,
   (d) 5 to 15 parts by weight of at least one compound which promotes cutaneous permeation selected from the group consisting of:
   crotamiton, and
   N-substituted 2-pyrrolidones of formula I,

wherein R represents a ($C_1$–$C_{15}$)-alkyl, cyclohexyl or 2-hydroxyethyl group,
   (e) 0,01 to 1 part by weight of antioxidant agent and,
   (f) 0,1 to 5 parts by weight of a hormone selected from the group consisting of oestrogen compounds, progestogen compounds and mixtures thereof.

2. A system as claimed in claim 1 wherein the plasticizing agent is oleic alcohol.

3. A system as claimed in claim 1 wherein the plasticizing agent is peglicol 5-oleate.

4. A system as claimed in claim 1 wherein the plasticizing agent is propylene glycol laurate.

5. A system as claimed in claim 1 wherein the plasticizing agent is a polypropoxyl ether of cetyl alcohol.

6. A system as claimed in claim 1 wherein the compound which promotes cutaneous permeation is selected from the group consisting of crotamiton and N-substituted 2-pyrrolidone compounds of formula I in which the R group represents a ($C_1$–$C_{15}$)-alkyl, cyclohexyl or 2-hydroxyethyl group.

7. A system as claimed in claim 1 wherein the poly(styrene-isoprene-styrene) triblock copolymer has a styrene content of between 14 and 50% by weight with respect to the weight of said copolymer.

8. A system as claimed in claim 1 wherein the oestrogen is 17-β-oestradiol.

9. A system as claimed in claim 1 wherein the progestogen is norethisterone acetate.

10. A system as claimed in claim 1 wherein its matrix contains per total 100 parts by weight:
    (a) 37.3 parts by weight of the poly(styrene-isoprene-styrene) triblock copolymer,
    (b) 38 parts by weight of tackifying resin,
    (c) 15 parts by weight of propylene glycol laurate,
    (d) 7 parts by weight of N-octyl-2-pyrrolidone,
    (e) 0.2 part by weight of a stabilizing agent,
    (f) 0.5 part by weight of 17-β-oestradiol, and
    (g) 2 parts by weight of norethisterone acetate.

11. A method for preparing a transdermal matrix system as claimed in claim 1, said method comprising:
    (α) mixing the SIS polymer, stabilizing agent and tackifying resin at a temperature higher than 110° C., then homogenizing the resulting mixture to form a first homogenous mixture;
    (β) incorporating into the first homogenous mixture the promoter(s) and the plasticizer at a temperature of between 80° and 110° C. then homogenizing the resulting mixture to form a second homogeneous mixture;

(γ) incorporating the second homogenous mixture with the hormone selected from the group consisting of estrogen compounds, progestogen compounds and mixtures thereof, then homogenizing the resulting mixture to form a third homogenous mixture;

(δ) coating the third homogenous mixture onto a temporary anti-adherent support in such manner as to obtain a coating on said support of 50 to 300 g/m²; and, (ε) transferring said coating to a final support.

12. A method for preparing a transdermal matrix system as claimed in claim 1, said method comprising:

(α) mixing the SIS polymer, stabilizing agent and then the tackifying resin in a solvent of said SIS polymer, at a temperature lower than the boiling point temperature of said solvent, then homogenizing the resulting mixture to obtain a first homogenous mixture;

(β) incorporating into the first homogenous mixture the promoter(s) and the plasticizer, then homogenizing the resulting mixture to form a second homogenous mixture;

(γ) incorporating into the second homogenous mixture the hormone selected from the group consisting of estrogen compounds, progestogen compounds and mixtures thereof, then homogenizing the resulting mixture to form a third homogenous mixture;

(δ) coating the third homogenous mixture, at room temperature, onto a temporary anti-adherent support in such manner as to obtain a coating on said support of 50 to 300 g/m², and, (ε) evaporating the solvent by heating said coating to a higher temperature than the boiling point temperature of said solvent, then transferring said coating to a final support.

13. A system as claimed in claim 5, wherein the plasticizing agent is a polypropoxyl ether of cetyl alcohol which contains 10 moles of propylene oxide per 1 mole of cetyl alcohol.

14. A system as claimed in claim 7, wherein the poly(styrene-isoprene-styrene) triblock copolymer has a styrene content of between 17 and 47% by weight with respect to the weight of said copolymer.

15. A method for preparing a transdermal matrix system as claimed in claim 10, said method comprising:

(α) mixing the SIS polymer, stabilizing agent and tackifying resin at a temperature higher than 110° C., to obtain a first homogeneous mixture;

(β) incorporating into the first homogenous mixture the promoter(s) and the plasticizer at a temperature of between 80° and 110° C. to obtain a second homogeneous mixture;

(γ) incorporating the second homogenous mixture the hormone selected from the group consisting of estrogen compounds, progestogen compounds and mixtures thereof to obtain a third homogenous mixture;

(δ) coating the third homogenous mixture onto a temporary anti-adherent support in such manner as to obtain a coating on said support of 50 to 300 g/m²; and, (ε) transferring said coating to a final support.

16. A method for preparing a transdermal matrix system as claimed in claim 10, said method comprising:

(α) mixing the SIS polymer, stabilizing agent and then the tackifying resin in a solvent of said SIS polymer, at a temperature lower than the boiling point temperature of said solvent to obtain a first homogenous mixture;

(β) incorporating into the first homogenous mixture the promoter(s) and the plasticizer to obtain a second homogenous mixture;

(γ) incorporating into the second homogenous mixture the hormone selected from the group consisting of estrogen compounds, progestogen compounds and mixtures thereof to obtain a third homogenous mixture;

(δ) coating the third homogenous mixture, at room temperature, onto a temporary anti-adherent support in such manner as to obtain a coating on said support of 50 to 300 g/m², and, (ε) evaporating the solvent by heating said coating to a higher temperature than the boiling point temperature of said solvent, then transferring said coating to a final support.

\* \* \* \* \*